United States Patent [19]
Ohtsuka

[11] Patent Number: 5,432,569
[45] Date of Patent: Jul. 11, 1995

[54] ILLUMINATION OPTICAL SYSTEM OF AN OPHTHALMOLOGIC INSTRUMENT

[75] Inventor: Hiroyuki Ohtsuka, Tokyo, Japan

[73] Assignee: Kabushiki Kaisha Topcon, Tokyo, Japan

[21] Appl. No.: 292,778

[22] Filed: Aug. 18, 1994

[30] Foreign Application Priority Data

Aug. 18, 1993 [JP] Japan .................................. 5-204001

[51] Int. Cl.⁶ .............................................. A61B 3/10
[52] U.S. Cl. ..................... 351/211; 351/206; 351/221
[58] Field of Search ............... 351/221, 211, 214, 205, 351/206

[56] References Cited

U.S. PATENT DOCUMENTS

4,770,523  9/1988  Yamada .................. 351/211

*Primary Examiner*—William L. Sikes
*Assistant Examiner*—Hung Xuan Dang
*Attorney, Agent, or Firm*—Finnegan, Henderson, Farabow, Garrett & Dunner

[57] ABSTRACT

An illumination optical system of an ophthalmologic instrument capable of avoiding the decrease of illumination efficiency without narrowing the width of a ring image formed on a pupil. The illumination optical system includes an illumination light source; a ring aperture plate for forming a ring slit image, with which a fundus of a subject's eye is illuminated, on the pupil of the eye; a conical prism disposed between the ring aperture plate and the illumination light source; and a scattering member disposed at a point substantially conjugate with the pupil.

9 Claims, 8 Drawing Sheets

PRIOR ART

ILLUMINATION OPTICAL SYSTEM OF AN OPHTHALMOLOGIC INSTRUMENT

BACKGROUND OF THE INVENTION

1. Field of the Invention

This invention relates to an illumination optical system of an ophthalmologic instrument which includes a ring aperture plate for forming a ring-shaped image on a pupil of a subject's eye and a conical prism disposed between the ring aperture plate and an illumination light source.

2. Description of the Prior Art

Figure 6:
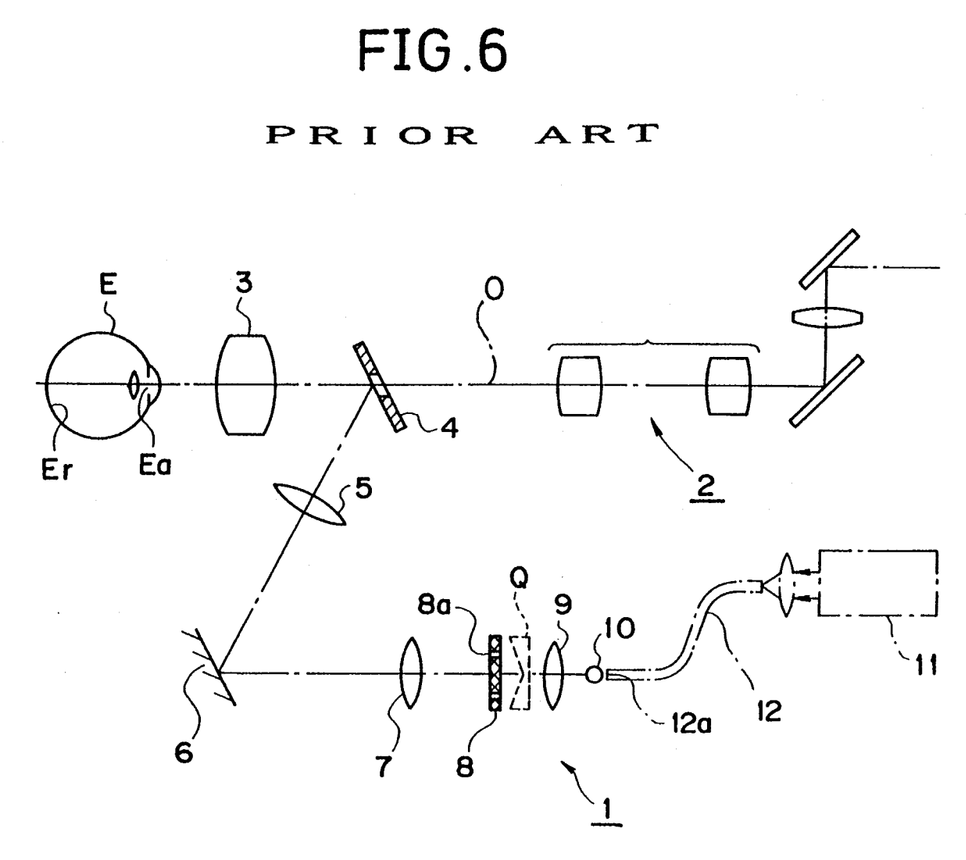
FIG. 6 is a schematic view showing optical systems of a conventional ophthalmologic instrument.

Heretofore, there is known an illumination optical system of an ophthalmologic instrument shown in FIG. 6. In FIG. 6, reference numeral 1 designates an illumination optical system for illuminating a fundus Er of a subject's eye E and reference numeral 2 designates an observation optical system for observing the fundus Er. The illumination optical system 1 includes an objective lens 3, a perforated mirror 4, a relay lens 5, a mirror 6, a relay lens 7, a ring aperture plate or ring-perforated plate 8, a condenser lens 9, and an illumination light source 10. The ring aperture plate 8 has a ring-shaped aperture 8a. The illumination light source 10 is conjugate with the ring aperture plate 8 with respect to the condenser lens 9. The ring aperture plate 8 is conjugate with the perforated mirror 4 with respect to the relay lenses 7 and 5. The perforated mirror 4 is conjugate with a pupil Ea of the eye E with respect to the objective lens 3.

Illumination light emitted by the illumination light source 10 reaches the eye E via the condenser lens 9, ring-shaped aperture 8a, relay lens 7, mirror 6, relay lens 5, perforated mirror 4, and objective lens 3. A ring image of the ring-shaped aperture 8a is formed on the pupil Ea. The fundus Er is illuminated with the illumination light which has formed this ring image and has passed through a peripheral portion of the pupil Ea.

The illumination light, or rather observation light reflected by the fundus Er passes through a central portion of the pupil Ea and reaches the observation optical system 2 via the objective lens 3 and the perforated mirror 4 since the pupil Ea and the perforated mirror 4 are conjugate with each other. Accordingly, the fundus Er is observed.

Figure 7:
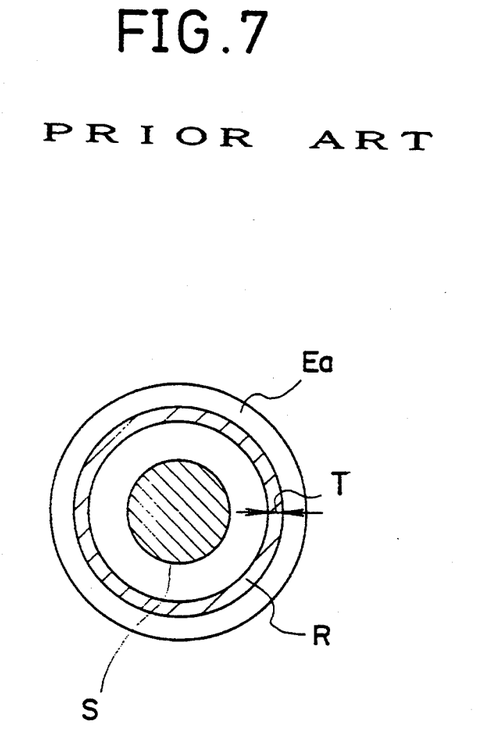
FIG. 7 is a descriptive drawing of a ring image formed on the pupil by means of the optical systems of the conventional ophthalmologic instrument.

As mentioned above, the illumination light reaches the eye E and passes through the peripheral portion of the pupil Ea to go to the fundus Er whereas the illumination light as the observation light is reflected by the fundus Er and passes through the central portion S of the pupil Ea (see FIG. 7) to go out of the eye E. For this reason, the illumination light and the observation light do not need to share a common optical path at an anterior portion of the eye E and therefore harmful light caused by reflection or scattering of the illumination light is removed at the anterior portion.

However, in the optical system of this type of conventional ophthalmologic instrument, the illumination light source 10, the ring aperture plate 8, the perforated mirror 4, and the pupil Ea are conjugate with each other. Accordingly, a filament image of the light source 10 is formed on the ring aperture plate 8.

Since only a part of the illumination light for forming the filament image, or only a part of the illumination light emitted by the illumination light source 10 passes through the ring-shaped aperture 8a, illumination efficiency is low. Accordingly, in order to raise the efficiency, an illumination optical system is proposed in which a conical prism Q shown by the broken line in FIG. 6 is disposed between the ring aperture plate 8 and the condenser lens 9 and thereby the illumination light emitted by the illumination light source 10 is changed into a ring-shaped beam of light to pass through the ring aperture plate 8a.

On the other hand, nowadays, in an ophthalmologic instrument for fluorescence photography, an optical system is proposed in which a laser source as the illumination light source is used. This optical system includes a laser source 11 and an optical fiber 12 for guiding a laser beam emitted by the laser source 11 which are each shown by the alternate long and short dash line in FIG. 6. An emission end 12a of the optical fiber 12 is located at the position of the illumination light source 10.

Figure 8:
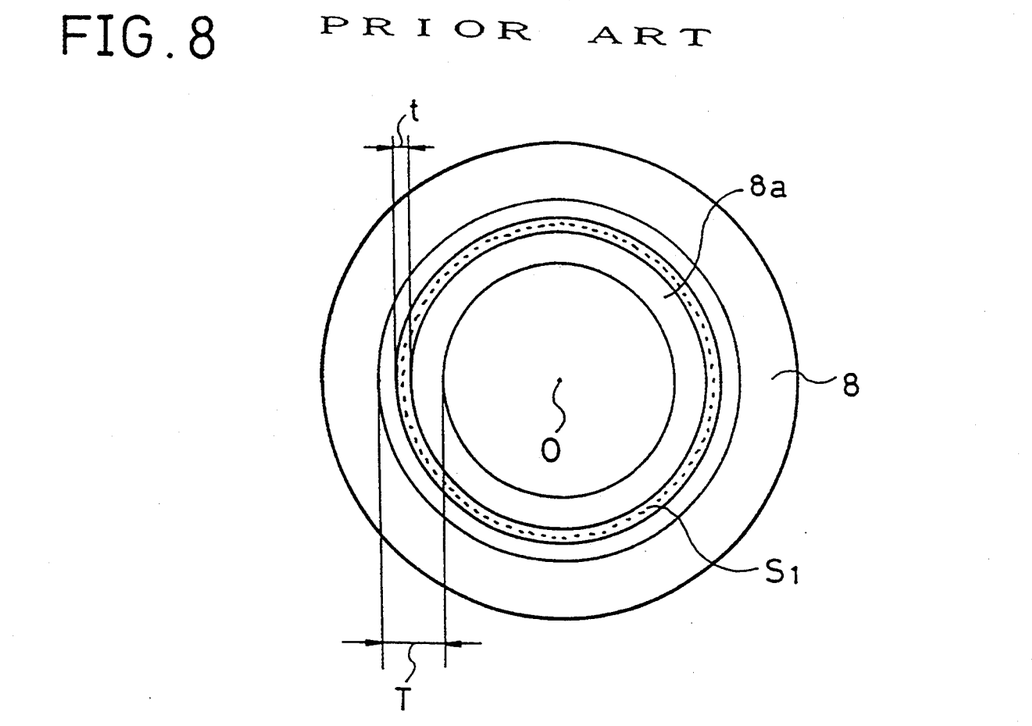
FIG. 8 is a plan view showing a relationship between a ring-shaped beam of light and a ring aperture plate in the conventional ophthalmologic instrument.

However, a core of the emission end 12a of the optical fiber 12 is extremely small in diameter. For example, it is 50 to 200 μm. Therefore, if a laser beam emitted from the emission end 12a is changed into a ring-shaped beam of light by means of the conical prism Q, on the pupil Ea is formed a ring image of the ring-shaped beam S1 a width t of which is much narrower than a width T of the ring-shaped aperture 8a as shown in FIG. 8. Accordingly, a width t' of the ring image becomes extremely narrow as shown in FIG. 9.

Therefore, a problem arises where slight misalignment brings about a cut-off state (c-shaped, reversed-c-shaped, or crescent-shaped state) of the ring-shaped beam S1 because a part of the ring-shaped beam S1 is intercepted by an edge Eb of the pupil Ea and accordingly the fundus Er is illuminated unevenly.

Figure 9:
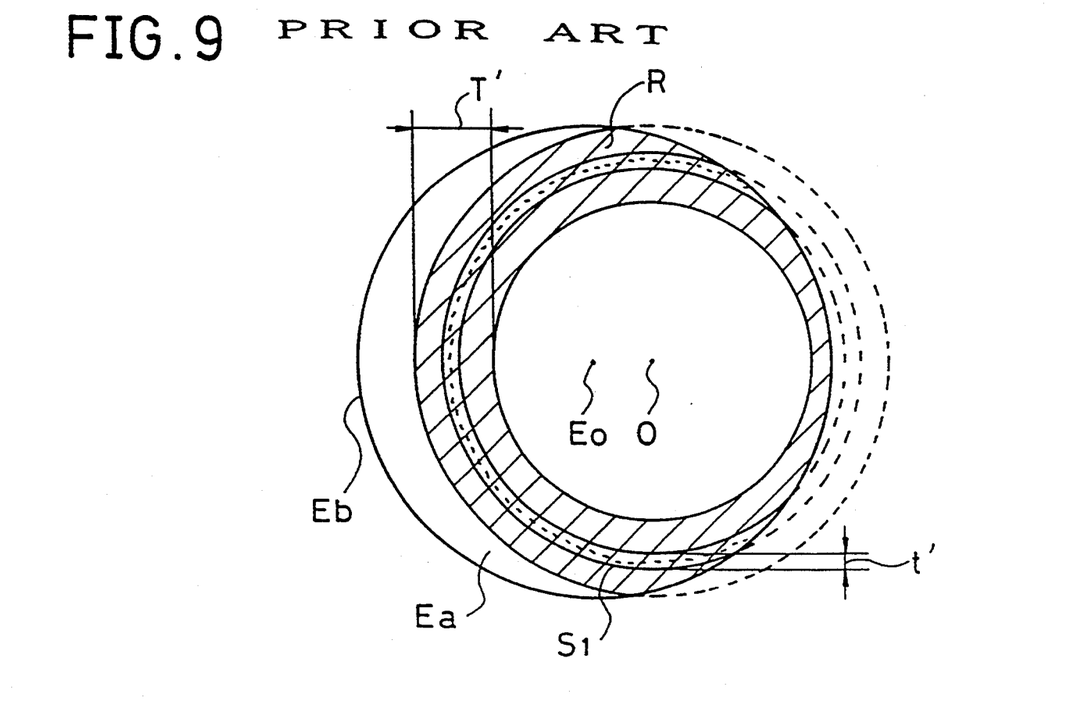
FIG. 9 is a descriptive drawing showing an example of drawbacks in the conventional ophthalmologic instrument.

That is, in the case of illumination light for forming a ring image R having the width T', the illumination light corresponding to an area shown by the slanted lines in FIG. 9 falls on the pupil Ea even if there is slight misalignment of the center Eo of the pupil Ea with respect to the center 0 of an optical axis of the observation optical system 2 in the up, down, right, and left directions. However, in the case of the ring-shaped beam S1 for forming a ring image having the width t', a part of the ring-shaped beam S1 is intercepted by the edge Eb of the pupil Ea (see the broken lines in FIG. 9) and, as a result, the fundus Er is not evenly illuminated with the ring-shaped beam S1.

It is a first object of the invention to provide an illumination optical system of an ophthalmologic instrument capable of avoiding the decrease of illumination efficiency without narrowing the width of a ring image formed on the pupil.

It is a second object of the invention to provide an illumination optical system of an ophthalmologic instrument capable of almost evenly illuminating the eye fundus regardless of slight misalignment.

It is a third object of the invention to provide an illumination optical system of an ophthalmologic instrument capable of forming a ring image on the pupil without narrowing the width of the ring image even in a case where a ring-shaped beam of light is made of illumination light emitted from an optical fiber small in diameter and falls on the fundus from the periphery of the pupil to illuminate the fundus.

SUMMARY OF THE INVENTION

To accomplish the above objects, the illumination optical system of the ophthalmologic instrument according to the invention includes an illumination light source, a ring aperture plate for forming a ring slit image with which the fundus of the eye is illuminated on the pupil of the eye, a conical prism disposed between the ring aperture plate and the illumination light source, and a scattering member disposed at a point substantially conjugate with the pupil.

Preferably, the scattering member is disposed between the ring aperture plate and the conical prism.

According to the invention, since the scattering member is disposed at the substantially conjugate point with the pupil, illumination light changed into a ring-shaped beam of light by means of the conical prism is scattered like a ring by means of the scattering member to illuminate a ring-shaped aperture of the ring aperture plate along the ring-shaped aperture.

Consequently, a width of a ring image formed on the pupil can be widened even if illumination light emitted by a light source small in diameter is changed into a ring-shaped beam of light small in width and is guided to the ring aperture plate. Therefore, the illumination light can be caused to enter the eye from the periphery of the pupil with the illumination light enclosing the pupil even if slight misalignment of the optical axis of the optical system of the instrument with the eye brings about a state in which a part of an image of the ring-shaped aperture is cut off by the pupil.

That is, according to the invention, a ring aperture image shaped like a crescent can be prevented, so that the fundus is almost evenly illuminated although a part of the illumination light entering the eye is intercepted because of the misalignment.

DETAILED DESCRIPTION OF THE PREFERRED EMBODIMENTS

First Embodiment

Figure 1:
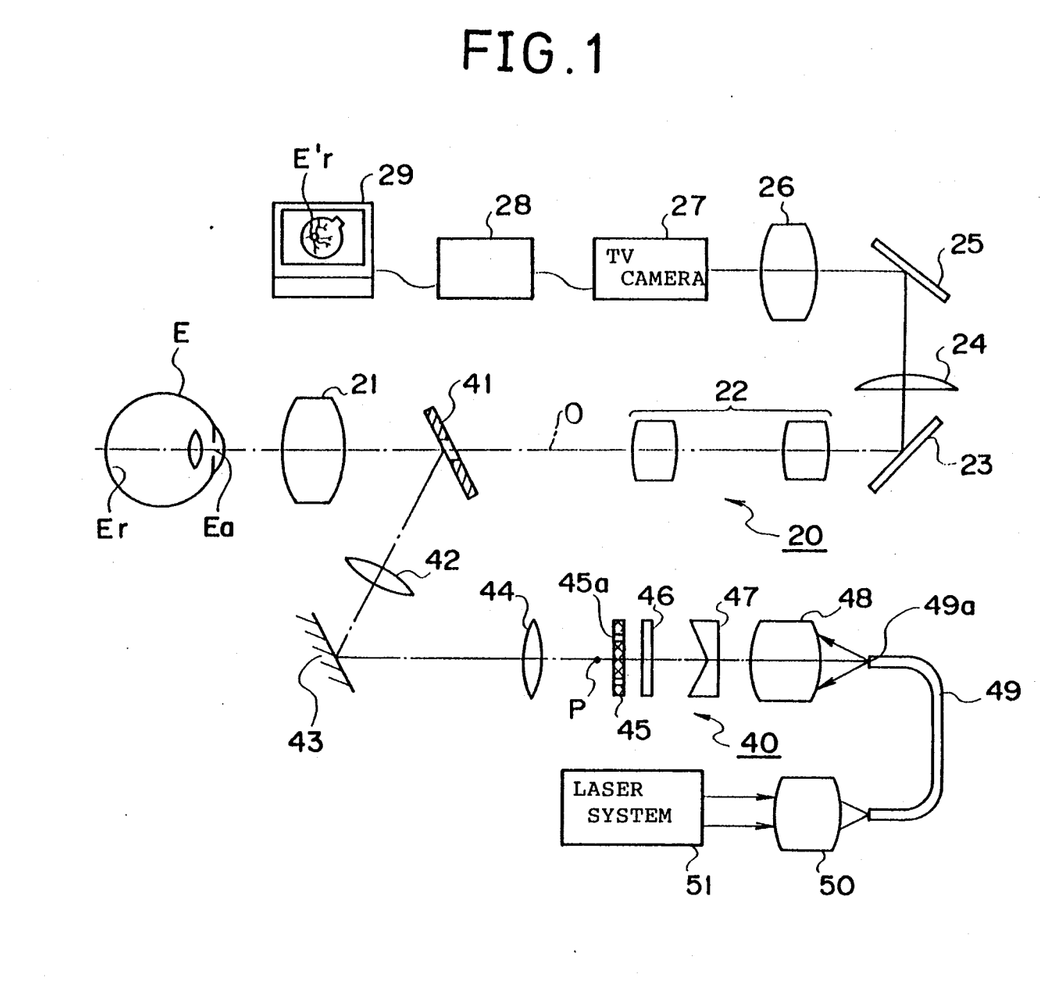
FIG. 1 is a schematic view showing optical systems of an ophthalmologic instrument according to the invention.

FIG. 1 is a schematic view showing an arrangement of optical systems of a fundus camera as an ophthalmologic instrument according to the invention.

In FIG. 1, numeral 20 designates a photographic optical system for photographing a fundus Er of a subject's eye and numeral 40 designates an illumination optical system for illuminating the fundus Er.

The photographic optical system 20 includes an objective lens 21 which faces the eye E, a focusing lens 22, a reflecting mirror 23, a field lens 24, a mirror 25, an image formation lens 26, and a TV camera 27. Numeral 28 designates an image processing unit and numeral 29 designates a monitor for displaying a fundus image photographed by the TV camera 27.

The illumination optical system 40 includes the objective lens 21, a perforated mirror 41, a relay lens 42, a mirror 43, a relay lens 44, a ring aperture plate 45 having a ring-shaped aperture 45a which is disposed at a point conjugate with a pupil Ea of the eye E, a scattering member 46 disposed at a point substantially conjugate with the pupil Ea, a conical prism 47 for generating a ring-shaped beam of light and illuminating the ring-shaped aperture 45a with the ring-shaped beam, a condenser lens 48, an optical fiber 49, an image formation lens 50, and a laser system 51. An emission end 49a of the optical fiber 49 is conjugate with a point P positioned a little before the ring aperture plate 45.

Figure 2:
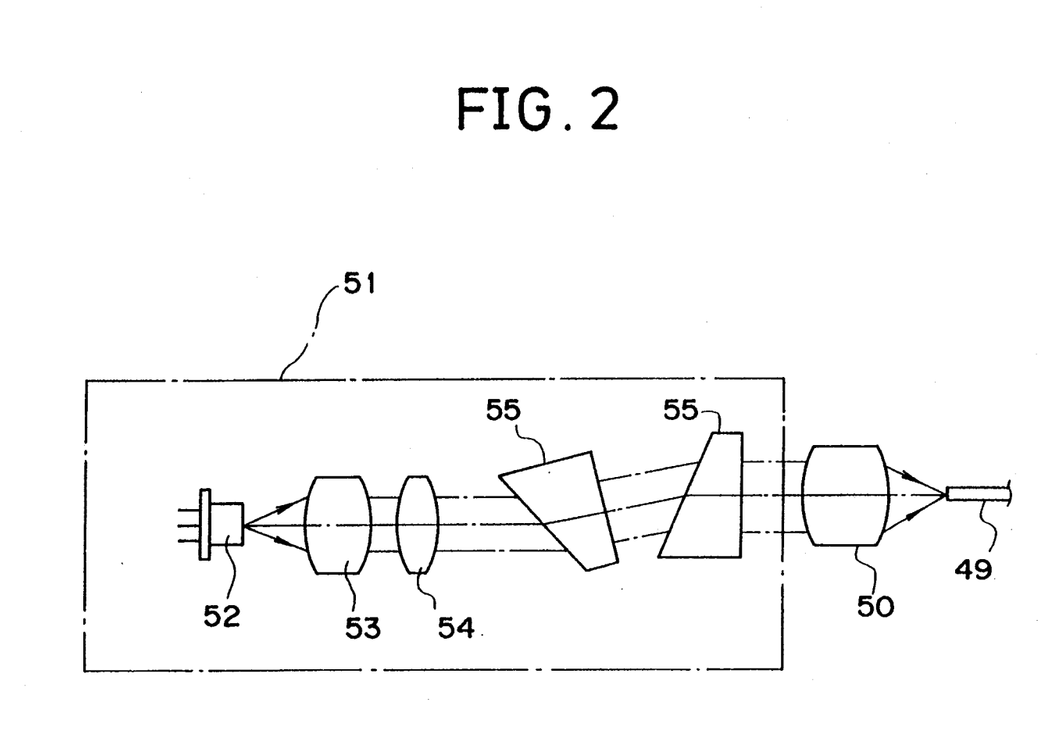
FIG. 2 is an optical diagram of a laser system.

As shown in FIG. 2, the laser system 51 includes a semiconductor laser 52, a collimator lens 53, a cylindrical lens 54 for correcting astigmatism, and a pair of anamorphic prisms 55, 55 for correcting the asymmetry of a spread angle of the semiconductor laser 52. A group of the cylindrical lens 54 and the anamorphic prisms 55, 55 serve to effectively guide a laser beam emitted by the semiconductor laser 52 to the optical fiber 49. In the case of a gas laser, the cylindrical lens 54 and the anamorphic prisms 55, 55 are not employed since a spread angle of the gas laser is small and is not asymmetric.

A description will now be given of the action of the ophthalmologic instrument mentioned above.

Figure 3:
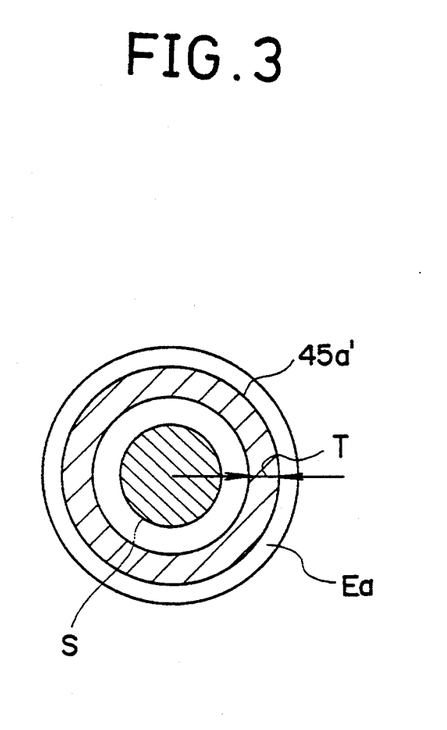
FIG. 3 is a descriptive drawing of a ring image formed on a pupil by means of the optical systems of the ophthalmologic instrument according to the invention.

When a main switch (not shown) is turned on, a laser beam is generated by the semiconductor laser 52 and is emitted from the laser system 51. The laser beam emitted from the laser system 51 is guided into the optical fiber 49 by means of the image formation lens 50. The laser beam traveling through the optical fiber 49 is emitted from the emission end 49a of the optical fiber 49. The laser beam emitted from the emission end 49a is condensed by the condenser lens 48. The condensed laser beam is changed into a ring-shaped beam of light by means of the conical prism 47. The ring-shaped beam is guided to the scattering member 46. The scattering member 46 illuminates wholly the ring-shaped aperture 45a with the ring-shaped beam along the ring-shaped aperture 45a. The illumination light which has passed through the ring-shaped aperture 45a strikes the eye E via the relay lens 44, mirror 43, relay lens 42, perforated mirror 41, and objective lens 21. Since the ring aperture plate 45 is conjugate with the pupil Ea, an image 45a' of the ring-shaped aperture 45a is formed on the pupil Ea, as shown in FIG. 3, and the fundus Er is illuminated with the ring aperture image 45a'.

At this time, the emission end 49a of the optical fiber 49 is conjugate with the point P positioned before the ring aperture plate 45 with respect to the condenser lens 48. Further, a ring-shaped beam of light having a broader width than that of the ring-shaped aperture 45a illuminates the ring aperture plate 45 by means of the scattering member 46 concentrically with the ring-shaped aperture 45a. That is, since the illumination light immediately after passing through the ring-shaped aperture 45a has the same ring width as that of the ring-shaped aperture 45a, the width T of a ring aperture image Ea' formed on the pupil Ea corresponds to the width of the ring-shaped aperture 45a regardless of the core of the emission end 49a of the optical fiber 49 having a very small diameter of 50~200 μm.

Therefore, even if the width of ring light formed by the conical prism 47 is narrow, the width of a ring aperture image Ea' formed on the pupil Ea becomes broad. Accordingly, even if slight misalignment of the optical axes of the optical systems of the instrument with the eye E brings about a state in which a part of the ring aperture image is cut off by the pupil, the illumination light can be caused to strike the eye E from the periphery of the pupil in a way that the pupil is surrounded by the illumination light.

In other words, although a part of illumination light falling on the eye E is intercepted because of the misalignment, a state can be prevented in which the ring aperture image Ea' is partially cut off and becomes crescent, and accordingly the fundus Er can be almost evenly illuminated.

The illumination light (observation light) reflected by the fundus Er reaches the TV camera 27 via the central portion S of the pupil Ea, objective lens 21, perforated mirror 41, focusing lens 22, mirror 23, field lens 24, and image formation lens 26. An eye fundus image Er' picked up by the TV camera 27 is displayed on the monitor 29 via the image processing unit 28.

Second Embodiment

Figure 4:
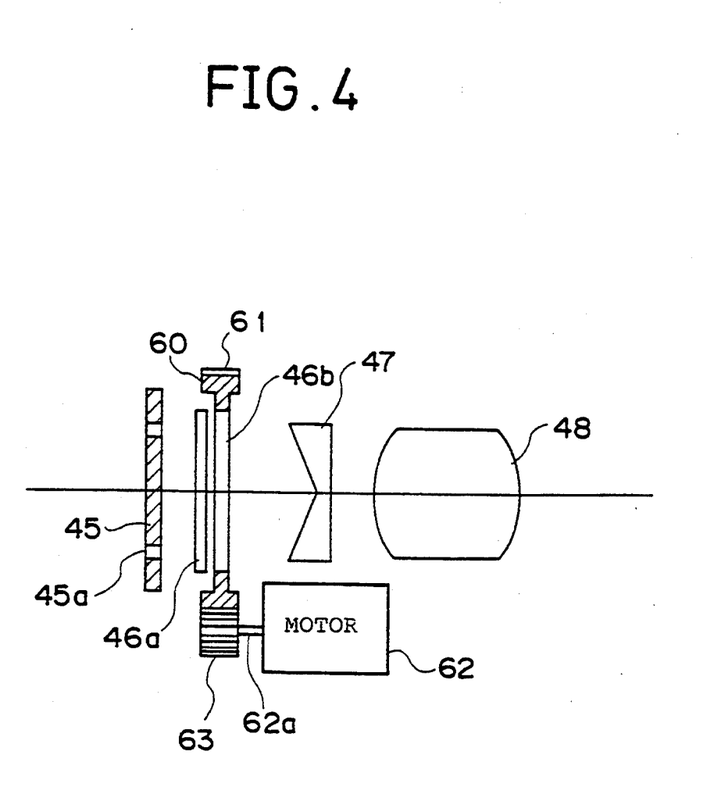
FIG. 4 is a descriptive drawing of a second embodiment.

FIG. 4 shows a second embodiment. In this embodiment, the scattering member 46 comprises two scattering plates 46a and 46b. The scattering plate 46a is stationary whereas the scattering plate 46b is rotated about the optical axis. In detail, the scattering plate 46b is fixed to a rotating ring 60. A gear 61 is formed around the rotating ring 60. The gear 61 is engaged with a gear 63 which is connected to a driving shaft 62a of a motor 62. By thus arranging them, scattering efficiency is improved. In the second embodiment, the scattering plate 46b is constructed to be rotated about the optical axis. Instead, the scattering plate 46b may be constructed to be reciprocated along the scattering plate 46a.

Third Embodiment

Figure 5:
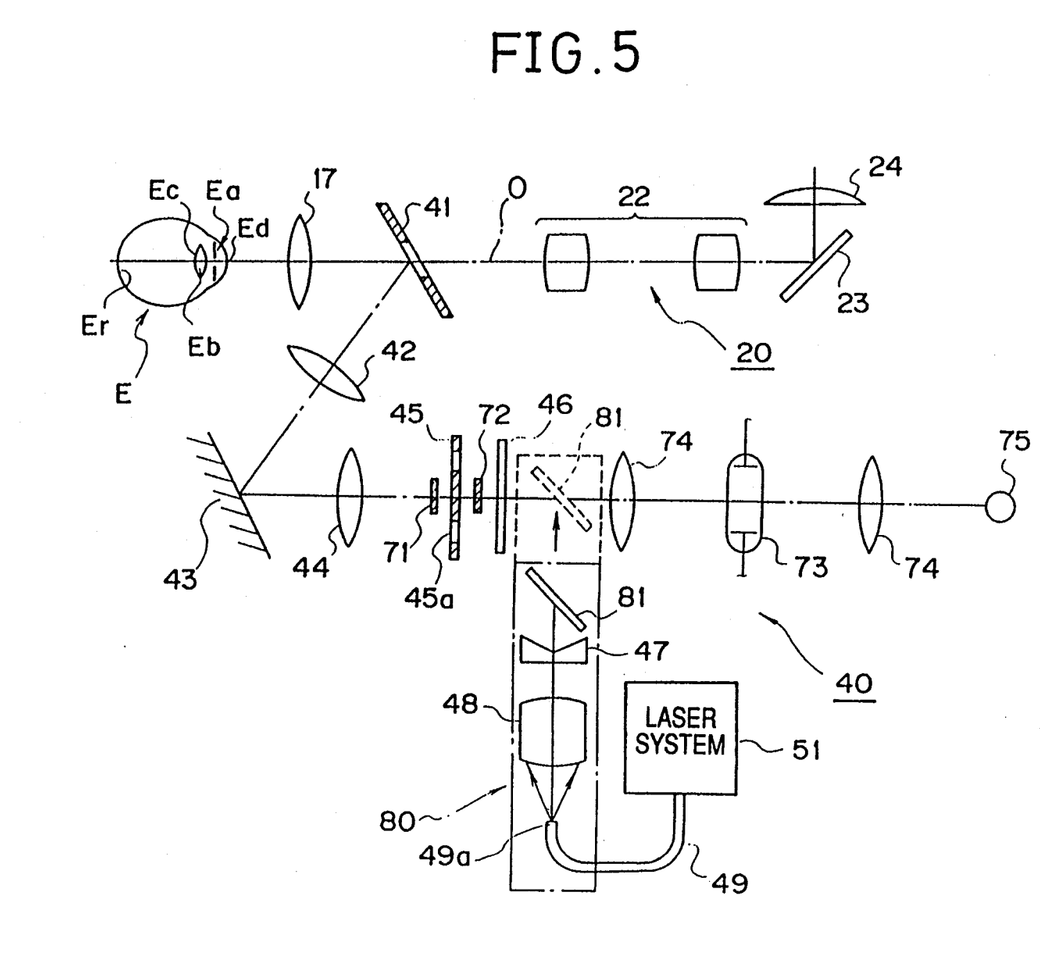
FIG. 5 is a descriptive drawing of a third embodiment.

FIG. 5 shows a third embodiment. In FIG. 5, numeral 71 designates a light intercepting plate small in diameter which is disposed at a conjugate point with a rear face Ec of a crystalline lens Eb, numeral 72 designates a light intercepting plate small in diameter which is disposed at a conjugate point with a cornea Ed, numeral 73 designates a xenon lamp, numeral 74 designates a condenser lens, and numeral 75 designates a halogen lamp. In addition, numeral 80 designates an optical unit including the scattering member 46, a mirror 81, the conical prism 47, the condenser lens 48, and the optical fiber 49. The scattering member 46 and the mirror 81 of the optical unit 80 are insertable into the optical path of the illumination optical system 40 as shown by the broken lines in FIG. 5 and are removable therefrom as shown by the continuous lines in FIG. 5. The emission end 49a of the optical fiber 49 is arranged to be conjugate with the ring aperture plate 45 when the scattering member 46 and the mirror 81 are inserted, as shown by the broken lines, in the optical path of the illumination optical system 40. The reason is that a distance between the scattering member 46 and the ring aperture plate 45 is maintained by the light intercepting plate 72 and, in addition, the whole of the ring-shaped aperture 45a is illuminated with ring-shaped scattered light generated by the scattering member 46.

In the above embodiments, the scattering member 46 is disposed between the ring aperture plate 45 and the conical prism 47. Instead, it may be disposed at any point except a point therebetween if the scattering member 46 is substantially conjugate with the pupil Ea.

What is claimed is:

1. An illumination optical system of an ophthalmologic instrument, comprising:
   an illumination light source;
   a ring aperture plate for forming a ring slit image on a pupil of a subject's eye, the ring slit image illuminating a fundus of the eye;
   a conical prism disposed between said ring aperture plate and said illumination light source; and
   a scattering member disposed at a point substantially conjugate with the pupil.

2. An illumination optical system of an ophthalmologic instrument according to claim 1, wherein said scattering member comprises two scattering plates one of which is stationary and the other is rotated about an optical axis of said illumination optical system.

3. An illumination optical system of an ophthalmologic instrument, comprising:
   an illumination light source;
   a ring aperture plate, disposed at a point substantially conjugate with a pupil of a subject's eye, for forming a ring slit image on the pupil, the ring slit image illuminating a fundus of the eye;
   a conical prism disposed between said ring aperture plate and said illumination light source; and
   a scattering member disposed between said ring aperture plate and said conical prism.

4. An illumination optical system of an ophthalmologic instrument according to claim 3, wherein said scattering member comprises two scattering plates one of which is stationary and the other is rotated about an optical axis of said illumination optical system.

5. An illumination optical system of an ophthalmologic instrument according to claim 3, wherein said scattering member comprises two scattering plates one of which is stationary and the other is reciprocated along said stationary scattering plate.

6. An illumination optical system of an ophthalmologic instrument, comprising:
   an illumination light source;
   a ring aperture plate, disposed at a point substantially conjugate with a pupil of a subject's eye, for forming a ring slit image on the pupil, the ring slit image illuminating a fundus of the eye;
   a conical prism, disposed between said ring aperture plate and said illumination light source, for changing illumination light emitted by said illumination light source into a ring-shaped beam of light; and
   a scattering member disposed between said ring aperture plate and said conical prism.

7. An illumination optical system of an ophthalmologic instrument according to claim 6, wherein said illumination light source comprises a laser source and an optical fiber for guiding a laser beam emitted by said laser source, an emission end of said optical fiber being disposed at a point substantially conjugate with said ring aperture plate.

8. An illumination optical system of an ophthalmologic instrument according to claim 6, wherein said illumination light source is an optical unit comprising a laser source and an optical fiber for guiding a laser beam emitted by said laser source, said optical unit being insertable into or removable from an optical path of said illumination optical system, an emission end of said optical fiber being disposed at a point conjugate with said ring aperture plate when said optical unit is inserted in the optical path.

9. An illumination optical system of an ophthalmologic instrument according to claim 6, wherein said illumination light source comprises a laser source and an optical fiber for guiding a laser beam emitted by said laser source, an emission end of said optical fiber, wherein the emission end of said optical fiber and said ring aperture plate are each disposed out of a point conjugate with each other.

* * * * *